(12) United States Patent
Ferree

(10) Patent No.: US 7,048,766 B2
(45) Date of Patent: May 23, 2006

(54) METHODS AND APPARATUS FOR TOTAL DISC REPLACEMENTS WITH OBLIQUE KEELS

(76) Inventor: Bret A. Ferree, 1238 Cliff Laine Dr., Cincinnati, OH (US) 45208

(*) Notice: Subject to any disclaimer, the term of this patent is extended or adjusted under 35 U.S.C. 154(b) by 0 days.

(21) Appl. No.: 10/860,920

(22) Filed: Jun. 4, 2004

(65) Prior Publication Data
US 2004/0249465 A1 Dec. 9, 2004

Related U.S. Application Data

(60) Provisional application No. 60/476,522, filed on Jun. 6, 2003.

(51) Int. Cl.
*A61F 2/28* (2006.01)

(52) U.S. Cl. ............... 623/17.16; 623/17.15; 606/61

(58) Field of Classification Search .. 623/17.11–17.16; 606/61
See application file for complete search history.

(56) References Cited

U.S. PATENT DOCUMENTS

| | | | |
|---|---|---|---|
| 4,759,769 A | 7/1988 | Hedman et al. ............... 623/17 |
| 5,002,576 A | 3/1991 | Fuhrmann et al. ............ 623/17 |
| 5,236,460 A | 8/1993 | Barber ........................ 623/17 |
| 5,258,031 A * | 11/1993 | Salib et al. ................. 623/17.15 |
| 5,314,477 A * | 5/1994 | Marnay ..................... 623/17.15 |
| 5,425,773 A | 6/1995 | Boyd et al. .................. 623/17 |
| 5,458,642 A | 10/1995 | Beer et al. .................. 623/17 |
| 5,507,816 A * | 4/1996 | Bullivant ................... 623/17.15 |
| 5,534,029 A | 7/1996 | Shima ......................... 623/17 |
| 5,562,738 A | 10/1996 | Boyd et al. .................. 623/17 |
| 5,824,094 A | 10/1998 | Serhan et al. ................. 623/17 |
| 5,888,226 A | 3/1999 | Rogozinski ................... 623/17 |
| 6,063,121 A | 5/2000 | Xavier et al. ................. 623/17 |
| 6,113,637 A | 9/2000 | Gill et al. .................... 623/17 |
| 6,113,638 A | 9/2000 | Williams et al. .............. 623/17 |
| 6,139,579 A | 10/2000 | Steffee et al. ................. 623/17 |
| 6,146,421 A * | 11/2000 | Gordon et al. ........... 623/17.15 |
| 6,228,118 B1 | 5/2001 | Gordon ....................... 623/17 |
| 2004/0158328 A1* | 8/2004 | Eisermann ............... 623/17.16 |

* cited by examiner

*Primary Examiner*—David J. Isabella
(74) *Attorney, Agent, or Firm*—Gifford, Krass, Groh, Sprinkle, Anderson & Citkowski, PC (57) ABSTRACT

Artificial disc replacement (ADR) systems with intradiscal components feature non anterior-posterior (A-P) or oblique-oriented keels such that the great vessels do not require as much retraction during insertion. The system may further include guides for aligning the ADR prior to insertion, and for cutting an oblique slot into a vertebral endplate to receive the keel. A screw adapted to penetrate a vertebral body may be used in conjunction with the keel. The screw and keel may converge, diverge or intersect. The screw may further include a mechanism providing a locking relationship with the keel. The system may further including a guide to direct drill bits and screws through holes in the keel. ADRs according to the invention may additionally, independently include a non-symmetrical endplate shaped so as to decrease the risk of injuring the great vessels. By virtue of the invention, a second ADR may be installed at a second level having a keel oriented differently from that of the ADR having an orientation other than anterior-to-posterior.

9 Claims, 9 Drawing Sheets

METHODS AND APPARATUS FOR TOTAL DISC REPLACEMENTS WITH OBLIQUE KEELS

REFERENCE TO RELATED APPLICATION

This application claims priority from U.S. Provisional Patent Application Ser. No. 60/476,522, filed Jun. 6, 2003, the entire content of which is incorporated herein by reference.

FIELD OF THE INVENTION

This invention relates generally to artificial disc replacements (ADRs) and, in particular, to ADRs with oblique keels.

BACKGROUND OF THE INVENTION

Eighty-five percent of the population will experience low back pain at some point. Fortunately, the majority of people recover from their back pain with a combination of benign neglect, rest, exercise, medication, physical therapy, or chiropractic care. A small percent of the population will suffer chronic low back pain. The cost of treatment of patients with spinal disorders plus the patient's lost productivity is estimated at 25 to 100 billion dollars annually.

Seven cervical (neck), 12 thoracic, and 5 lumbar (low back) vertebrae form the normal human spine. Intervertebral discs reside between adjacent vertebra with two exceptions. First, the articulation between the first two cervical vertebrae does not contain a disc. Second, a disc lies between the last lumbar vertebra and the sacrum (a portion of the pelvis).

The spine supports the body, and protects the spinal cord and nerves. The vertebrae of the spine are also supported by ligaments, tendons, and muscles which allow movement (flexion, extension, lateral bending, and rotation). Motion between vertebrae occurs through the disc and two facet joints. The disc lies in the front or anterior portion of the spine. The facet joints lie laterally on either side of the posterior portion of the spine.

The human intervertebral disc is an oval to kidney bean shaped structure of variable size depending on the location in the spine. The outer portion of the disc is known as the annulus fibrosis. The annulus is formed of 10 to 60 fibrous bands. The fibers in the bands alternate their direction of orientation by 30 degrees between each band. The orientation serves to control vertebral motion (one half of the bands tighten to check motion when the vertebra above or below the disc are turned in either direction). The annulus contains the nucleus. The nucleus pulpous serves to transmit and dampen axial loads. A high water content (70–80 percent) assists the nucleus in this function. The water content has a diurnal variation. The nucleus imbibes water while a person lies recumbent. Activity squeezes fluid from the disc. Nuclear material removed from the body and placed into water will imbibe water swelling to several times its normal size. The nucleus comprises roughly 50 percent of the entire disc. The nucleus contains cells (chondrocytes and fibrocytes) and proteoglycans (chondroitin sulfate and keratin sulfate). The cell density in the nucleus is on the order of 4,000 cells per micro liter.

Interestingly, the adult disc is the largest avascular structure in the human body. Given the lack of vascularity, the nucleus is not exposed to the body's immune system. Most cells in the nucleus obtain their nutrition and fluid exchange through diffusion from small blood vessels in adjacent vertebra.

The disc changes with aging. As a person ages the water content of the disc falls from approximately 85 percent at birth to 70 percent in the elderly. The ratio of chondroitin sulfate to keratin sulfate decreases with age. The ratio of chondroitin 6 sulfate to chondroitin 4 sulfate increases with age. The distinction between the annulus and the nucleus decreases with age. These changes are known as disc degeneration. Generally disc degeneration is painless.

Premature or accelerated disc degeneration is known as degenerative disc disease. A large portion of patients suffering from chronic low back pain are thought to have this condition. As the disc degenerates, the nucleus and annulus functions are compromised. The nucleus becomes thinner and less able to handle compression loads. The annulus fibers become redundant as the nucleus shrinks. The redundant annular fibers are less effective in controlling vertebral motion. The disc pathology can result in: 1) bulging of the annulus into the spinal cord or nerves; 2) narrowing of the space between the vertebra where the nerves exit; 3) tears of the annulus as abnormal loads are transmitted to the annulus and the annulus is subjected to excessive motion between vertebra; and 4) disc herniation or extrusion of the nucleus through complete annular tears.

Current surgical treatments of disc degeneration are destructive. One group of procedures removes the nucleus or a portion of the nucleus; lumbar discectomy falls in this category. A second group of procedures destroy nuclear material; Chymopapin (an enzyme) injection, laser discectomy, and thermal therapy (heat treatment to denature proteins) fall in this category. A third group, spinal fusion procedures either remove the disc or the disc's function by connecting two or more vertebra together with bone. These destructive procedures lead to acceleration of disc degeneration. The first two groups of procedures compromise the treated disc. Fusion procedures transmit additional stress to the adjacent discs. The additional stress results in premature disc degeneration of the adjacent discs.

Prosthetic disc replacement offers many advantages. The prosthetic disc attempts to eliminate a patient's pain while preserving the disc's function. Current prosthetic disc implants, however, either replace the nucleus or the nucleus and the annulus. Both types of current procedures remove the degenerated disc component to allow room for the prosthetic component. Although the use of resilient materials has been proposed, the need remains for further improvements in the way in which prosthetic components are incorporated into the disc space, and in materials to ensure strength and longevity. Such improvements are necessary, since the prosthesis may be subjected to 100,000,000 compression cycles over the life of the implant.

Artificial disc replacements (ADRs) are generally inserted into anterior portion of the spine through a transabdominal or retroperitoneal approach. The great vessels; aorta, vena cava, iliac vein, and iliac artery lie on the anterior aspect of the lumbar spine. Prior-art ADRs with anterior-to-posterior oriented keels requires insertion of the ADR from a direct anterior approach to the spine. The great vessels must be retracted be retracted from the anterior portion of the spine to insert the ADRs. Retraction of the great vessels is difficult and dangerous. The danger increases the further the vessels are retracted. The vessels must retracted almost completely off the anterior portion of the spine when inserting ADRs with anterior to posterior directed keels.

SUMMARY OF THE INVENTION

This invention improves upon the prior art by providing ADR systems with intradiscal components having non anterior-posterior (A-P) or oblique-oriented keels. By allowing such components to be inserted in an oblique direction, the great vessels do not require as much retraction during insertion. In addition to traditional methods, navigational systems may be used to help align components with oblique-oriented keels. Such systems are well known to those skilled in the art and include, for example, the Steath System by Medtronic Sofamor Danek could be utilized.

An artificial disc replacement (ADR) system according to the invention broadly comprises an intradiscal component including an anterior portion, a posterior portion, and a keel adapted to penetrate a vertebral endplate, the keel having an orientation other than anterior-to-posterior when the component is installed.

The system may further include a guides for aligning the ADR prior to insertion, and for cutting an oblique slot into a vertebral endplate to receive the keel. A screw adapted to penetrate a vertebral body may be used in conjunction with the keel. The screw and keel may converge, diverge or intersect. The screw may further include a mechanism providing a locking relationship with the keel. The system may further including a guide to direct drill bits and screws through holes in the keel.

By virtue of the invention, a second ADR may be installed at a second level having a keel oriented differently from that of the ADR having an orientation other than anterior-to-posterior. ADRs according to the invention may additionally, independently include a non-symmetrical endplate shaped so as to decrease the risk of injuring the great vessels.

DETAILED DESCRIPTION OF THE INVENTION

Figures 1A, 1B, 1C, 2A, 2B:
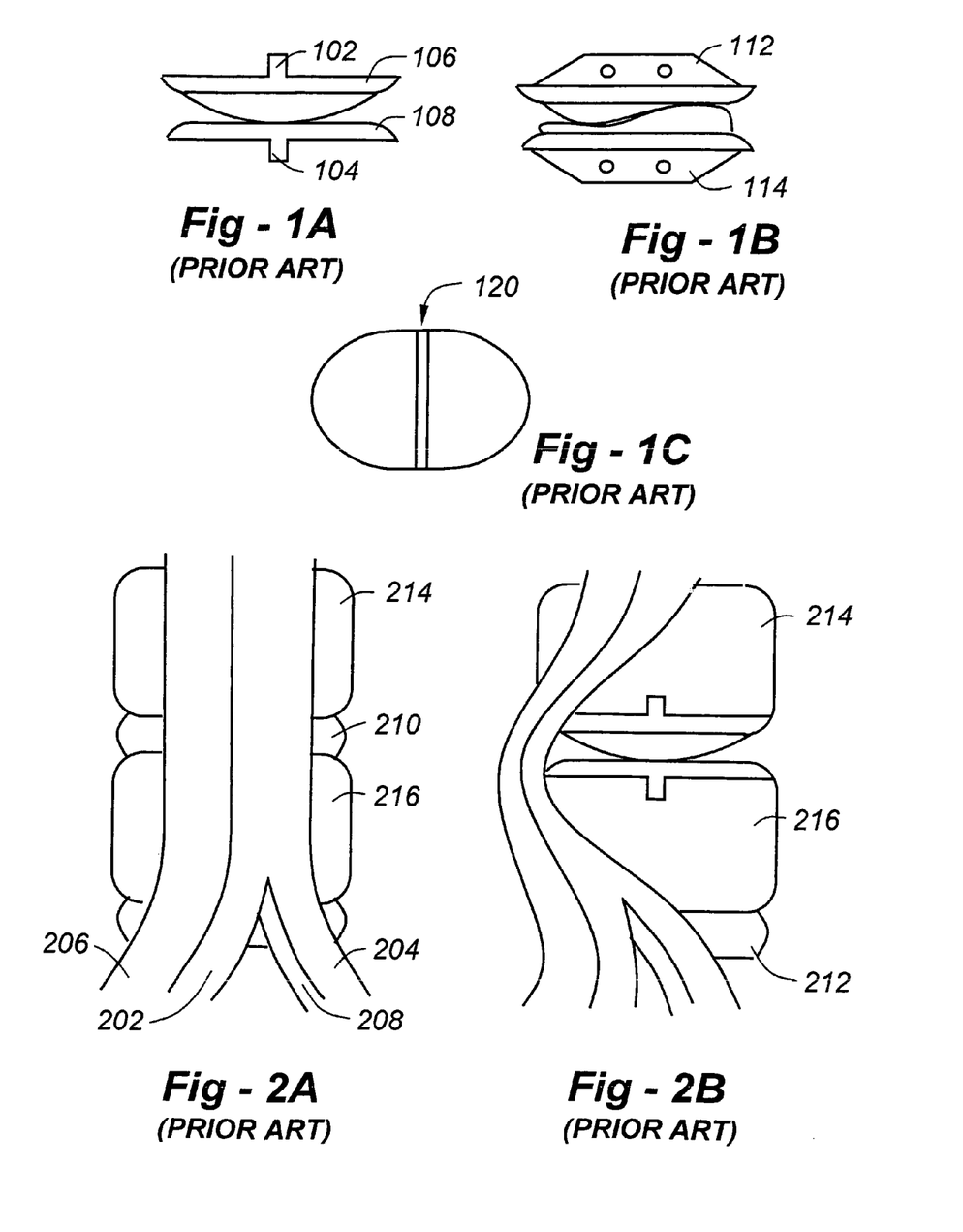
FIG. 1A is a view of the anterior aspect of a prior-art TDR.
FIG. 1B is a view of the side of a prior-art TDR with anterior to posterior oriented keels.
FIG. 1C is a view of the vertebral side of a prior-art TDR endplate.
FIG. 2A is a view of the anterior aspect of the lumbar spine and the great vessels overlying the spine.
FIG. 2B is a view of the anterior aspect of the lumbar spine, the great vessels, and a prior art TDR.

FIG. 1A is a view of the anterior aspect of a prior-art ADR. The anterior-to-posterior (A-P) oriented keels 102, 104 are represented by the projections from the top and bottom ADR endplates 106, 108. FIG. 1B is a view of the side of a prior-art ADR with anterior to posterior oriented keels 112, 114. The keels are represented by the trapezoidal shaped projections from the top and bottom ADR endplates. FIG. 1C is a view of the vertebral side of a prior-art ADR endplate. The keel is represented by area 120 of the drawing that courses from the top (posterior aspect of the ADR) to the bottom (anterior aspect of the ADR) of the drawing.

FIG. 2A is a view of the anterior aspect of the lumbar spine and the great vessels overlying the spine. The aorta and iliac arteries are indicated at 202, 204, and the vena cava and iliac veins are indicated at 206, 208. Intervertebral discs are shown at 210, 212, and vertebrae are shown at 214, 216. FIG. 2B is a view of the anterior aspect of the lumbar spine, the great vessels, and a prior-art ADR. The drawing illustrates the great vessel retraction required to insert the prior-art ADR. The drawing shows the great vessels retracted to the left of the drawing.

Figure 3A:
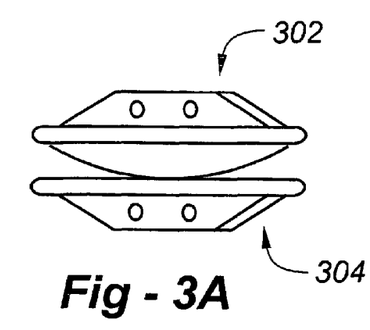
FIG. 3A is a view of the anterior aspect of a TDR with novel, oblique, oriented keels.
Figure 3B:
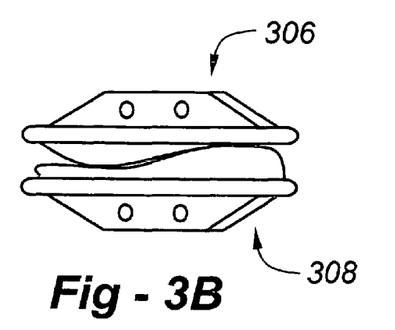
FIG. 3B is a view of the lateral side of a TDR with novel, oblique, oriented keels.
Figures 3C, 4A, 4B:
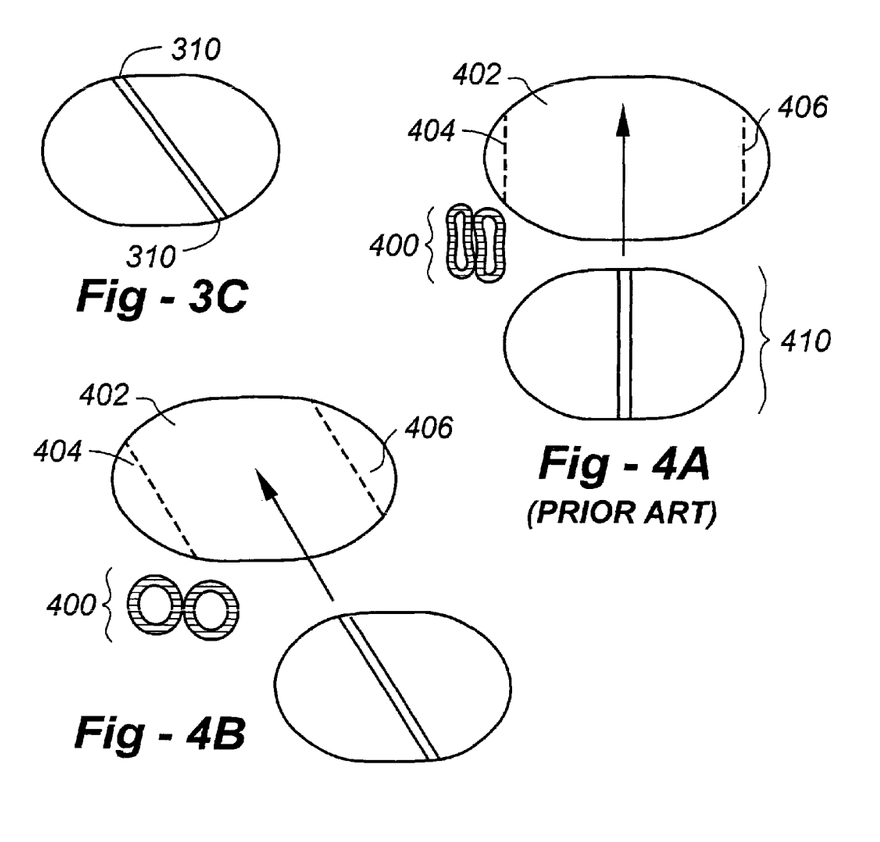
FIG. 3C is a view of the vertebral surface of a TDR with novel, oblique, oriented keel.
FIG. 4A is an axial cross section of the spine and a prior-art TDR.
FIG. 4B is an axial cross section of the spine and a TDR with oblique oriented keels.

FIG. 3A is a view of the anterior aspect of an ADR according to the invention having oblique (i.e., non-AP) oriented keels 302, 304. FIG. 3B is a view of the lateral side of a ADR oblique-oriented keels 306, 308. FIG. 3C is a view of the vertebral surface of an ADR with oblique-oriented keel 310.

FIG. 4A is an axial cross section of the spine and a prior-art ADR 410. The great vessels are drawn in their retracted position on the left side of the drawing (400). The disc space is shown at 402 with an arrow and dotted lines 404, 406 that represent the edges of a channel needed to insert the ADR 410. The arrow represents the direction of ADR insertion. FIG. 4B is an axial cross section of the spine and an ADR with oblique oriented keels. The drawing shows the novel ADR can be inserted with less great vessel retraction. The vessels can remain over a larger portion of the anterior aspect of the spine. The drawing also illustrates the vessels are less compressed when they are retracted less.

Figures 5A, 5B, 6A, 6B:
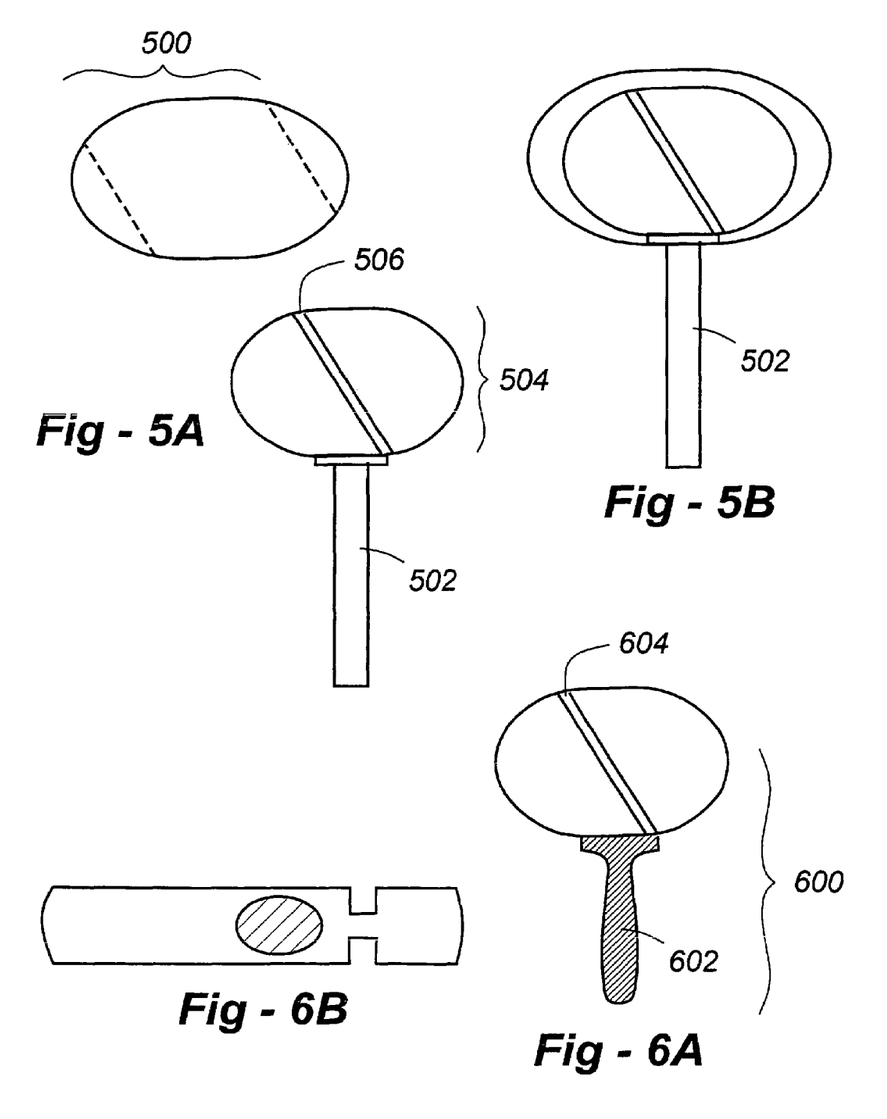
FIG. 5A is an axial cross section of a disc space, a TDR with oblique keels, and a removal alignment guide.
FIG. 5B is an axial cross section of the disc space drawn in FIG. 5A.
FIG. 6A is the view of the top of a novel guide to cut slots for the oblique keels.
FIG. 6B is a view of the front of the novel guide drawn in FIG. 6A.

FIG. 5A is an axial cross section of a disc space 500, an ADR 504 with an oblique keel 506, and a removal alignment guide 502. FIG. 5B is an axial cross section of the disc space drawn in FIG. 5A, and the ADR of 5A inserted into the disc space. The position of the ADR can be checked by the orientation and position of the alignment guide. For example, the alignment guide may be located in the center of the disc space from the left to right, and perpendicular to the vertebra when the ADR is placed properly. The orientation of the alignment guide can be confirmed by direct view, x-ray, fluoroscopy, CT scan, or MRI. The alignment guide could be reversibly attached to the ADR. For example, the alignment guide could be screwed to the ADR endplate.

FIG. 6A is the view of the top of a guide 600 having a handle 602 and one or more grooves 604 used to cut slots for the oblique keels. The area 602 represents an oblique groove on the top of the guide. FIG. 6B is a view of the front of the novel guide drawn in FIG. 6A. The guide is inserted into the disc space via an oblique course. The position of the guide may be checked as outlined in FIG. 5B. For example, surgeons can use x-ray, fluoroscopy, CT scan, or MRI to confirm the proper position and orientation of the guide. Once the guide is aligned properly, a cutting instrument such as an osteotome, drill, or saw can be inserted into the grooves 602 of the guide. The cutting instrument is advanced into the guide to from oblique slots in the vertebrae. The cutting instrument may have a depth stop that prevents cutting through the back of the vertebra. Alternatively, the slot within the cutting guide could end prior to the end of the guide.

Figure 6C:
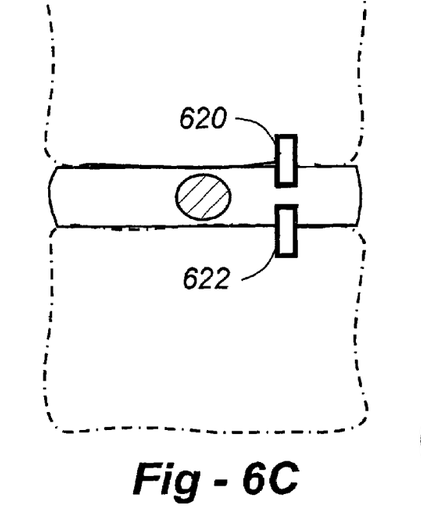
FIG. 6C is a view of the anterior aspect of the spine and the novel cutting guide.
Figure 6D:
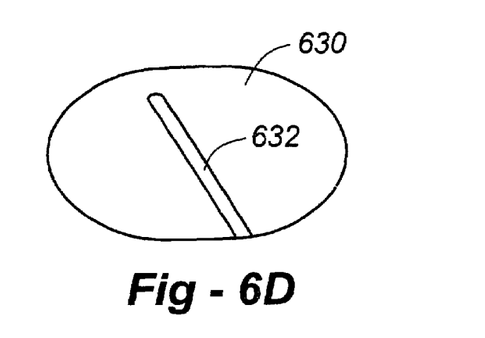
FIG. 6D is a view of the endplate of a vertebrae.
Figure 6E:
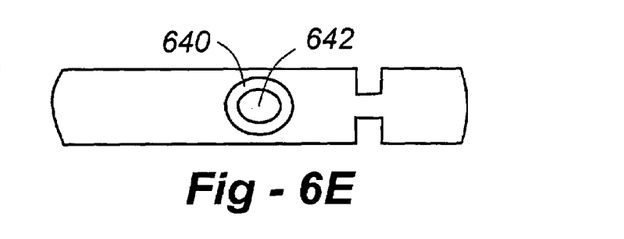
FIG. 6E is a view of the front of an alternative cutting guide to that drawn in FIG. 6B.

FIG. 6C is a view of the anterior aspect of the spine and the novel cutting guide. The areas 620, 622 of the drawing represent the anterior aspect of slots cut into the vertebrae using the cutting guide described in FIG. 6C. FIG. 6D is a view of the endplate of vertebrae 630 showing an oblique slot 632. FIG. 6E is a view of the front of an alternative cutting guide to that drawn in FIG. 6B having a partially radio-opaque handle 640. The center 642 of the handle is radio-lucent. The hole within the guide, that receives the handle, courses through the guide. When aligned properly, an x-ray directed from anterior to posterior, shows the radio-opaque circle within the handle, centered in the hole in the guide that receives the handle.

Figure 6F:
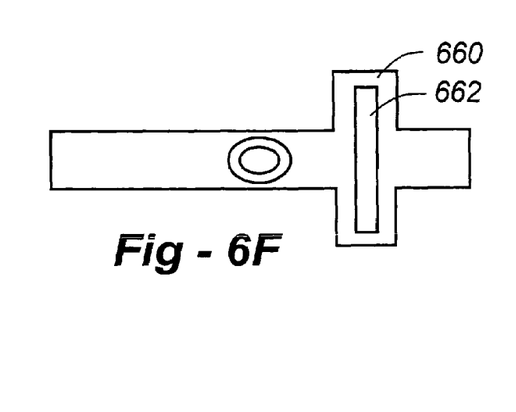
FIG. 6F is a view of the front of an alternative cutting guide to that drawn in FIG. 6E.
Figure 6G:
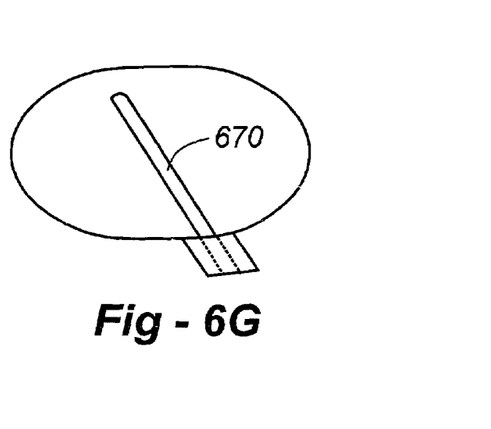
FIG. 6G is a view of the top of the embodiment of the cutting guide drawn in FIG. 6F.

FIG. 6F is a view of the front of an alternative cutting guide including a single slot 660 that courses obliquely through the cutting guide. Slots are created in both vertebrae at the same time by inserting a cutting instrument into the guide. The front of the guide has a window 662 that directs the cutting instrument into the slot in the guide. FIG. 6G is a view of the top of the embodiment of the cutting guide drawn in FIG. 6F used to form slot 670. The projection from the bottom of the guide represents the window 622 on the front of the guide. The window portion of the guide sits outside the disc space. The extradiscal location of the raised window, allows the guide to be rotated in the disc space. The dotted lines within the raised window of the guide represent the oblique course of the walls of the window.

Figure 7:
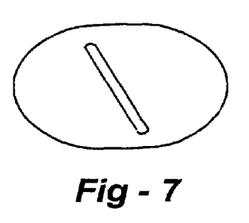
FIG. 7 is a view of the top of an alternative embodiment of the ADR.

FIG. 7 is a view of the top of an alternative, asymmetric embodiment of an ADR according to the invention. A portion of the ADR on the left side of the drawing has been removed. The reduced profile of the ADR facilitates passage of the ADR by the great vessels during insertion of the ADR into the disc space.

Figure 8A:
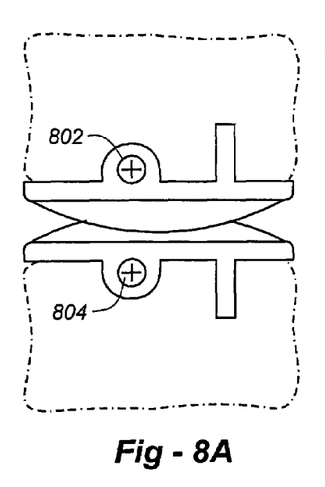
FIG. 8A is an anterior view of the spine and an alternative embodiment of the ADR drawn in FIG. 3A.
Figure 8B:
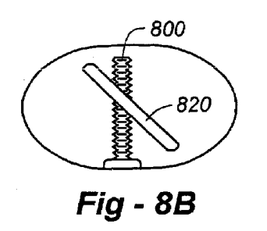
FIG. 8B is a view of the top of the ADR drawn in FIG. 8A.

FIG. 8A is an anterior view of the spine and an alternative embodiment of an ADR having screws 802, 804 that help hold the ADR in the disc space. FIG. 8B is a view of the top of the ADR drawn in FIG. 8A. A screw 800 passes through the front of the ADR and an oblique keel 820. The convergence of the screw and the keel resist extrusion of the ADR in a direction parallel to the keel.

Figure 8C:
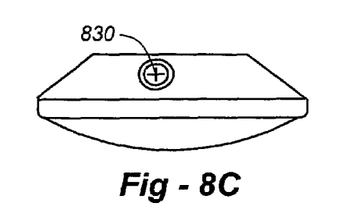
FIG. 8C is a lateral view of the upper half of the ADR drawn in FIG. 8B.
Figure 8D:
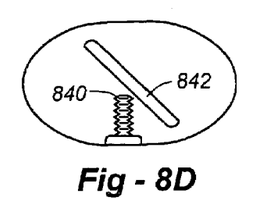
FIG. 8D is view of the top of an alternative embodiment of the ADR drawn in FIG. 8B.
Figure 8E:
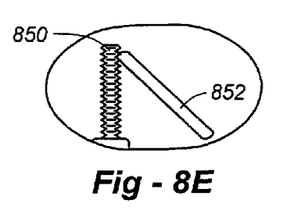
FIG. 8E is a view of the top of an alternative embodiment.

FIG. 8C is a lateral view of the upper half of the ADR drawn in FIG. 8B. A cross section 830 of the screw can be seen in a hole in the keel. FIG. 8D is view of the top of an alternative embodiment of an ADR having a screw 840 that does not pass through keel 842. FIG. 8E is a view of the top of a further embodiment wherein a screw 850 and keel 852 converge, but the screw does not pass through the keel.

Figure 8F:
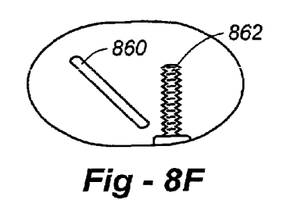
FIG. 8F is a view of the top of an alternative embodiment of the ADR drawn in FIG. 8B.
Figure 8G:
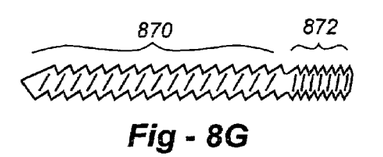
FIG. 8G is a lateral view of one embodiment of the screw drawn in FIG. 8B.

FIG. 8F is a view of the top of an alternative embodiment wherein the screw 860 and the keel 862 diverge. FIG. 8G is a lateral view of an embodiment of a screw having a coarse thread pattern 870 on the portion of the screw that rests in the vertebra. The thread pattern 872 is finer in the area of the screw that lies in the ADR. A single thread could be chased on the coarse portion of the thread. Multiple threads could be traced in the ADR portion of the screw. The screw may be tightened to the ADR without stripping out the threads in the vertebra. The tight fit between the screw and the ADR prevent the screw from backing out of the ADR. Alternatively, the threads of the screw could be slightly different than the threads in the ADR. The threads of the screw could strip slightly as the screw is tightened in the ADR, thus locking the screw to the ADR.

Figure 8H:
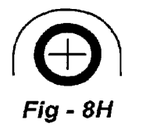
FIG. 8H is an anterior view of an alternative locking mechanism to prevent screws from backing out of the ADR drawn in FIG. 8B.

FIG. 8H is an anterior view of an alternative locking mechanism to prevent screws from backing out of the ADR. A C-ring within the ADR expands as the head of the screw passes through the C-ring. The C-ring contracts after the head of the screw has passed through the C-ring, thus locking the screw in the ADR.

Figure 8I:
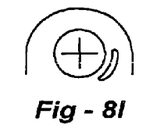
FIG. 8I is an anterior view of an alternative locking mechanism to prevent screws form backing out of the ADR drawn in FIG. 8B.
Figure 8J:
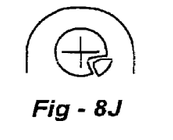
FIG. 8J is an anterior view of the locking mechanism drawn in FIG. 8I.

FIG. 8I is an anterior view of an alternative locking mechanism to prevent screws form backing out of the ADR. A screw has been placed in a hole in the ADR. FIG. 8J is an anterior view of the locking mechanism drawn in FIG. 8I. A tool has been inserted and rotated within the slot adjacent to the hole for the screw in the ADR. The thin bridge of ADR between the holes has been deformed by the tool. A portion of the ADR blocks the screw from backing out of the ADR.

Figure 9A:
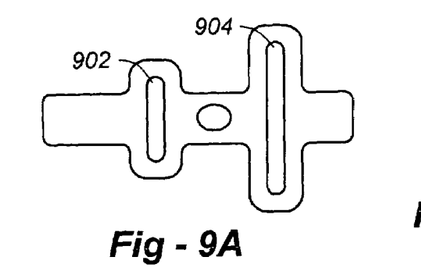
FIG. 9A is an anterior view of an alternative embodiment of the guide drawn in FIG. 6F.

FIG. 9A is an anterior view of an alternative embodiment of a guide having two slots 902, 904. The smaller slot 902 is designed to guide a router-like bit. The router-like bit mills a recess. The recess accepts the portion of the ADR that holds the screw. The longer slot 904 accepts a saw blade used to cut a slot for the oblique keel. Prior art slots are created with chisels which may cause microfractures and lead to a complete fracture of a vertebra. Cutting bone with drill bits, router bits, and saw blades help to preserve the strength of the vertebrae.

Figures 9B, 9C:
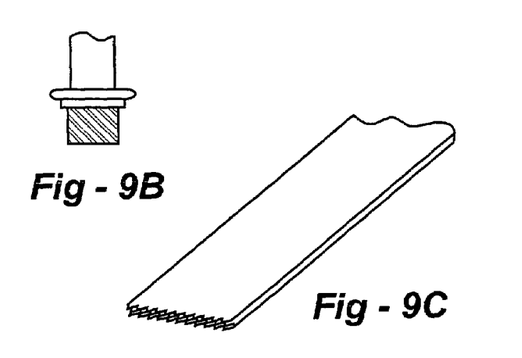
FIG. 9B is a lateral view of a router bit.
FIG. 9C is an oblique view of a saw blade.
Figure 9D:
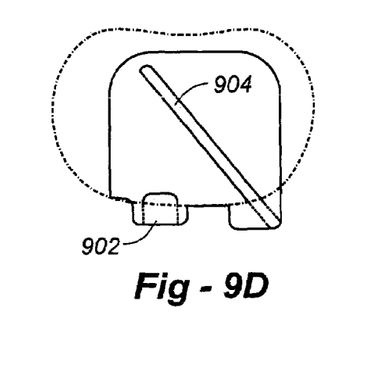
FIG. 9D is an axial cross section of the disc and the embodiment of the guide drawn in FIG. 9A.

FIG. 9B is a lateral view of a router bit. The dotted area of the drawing represents a collar. The collar cooperates with the slot of the guide to create a recessed area in the vertebrae. FIG. 9C is an oblique view of a saw blade. The saw blade cooperates with the larger slot in the guide to create a slot for the ADR keels. FIG. 9D is an axial cross section of the disc and the embodiment of the guide drawn in FIG. 9A. The dotted area represents opening in the guide.

Figure 9E:
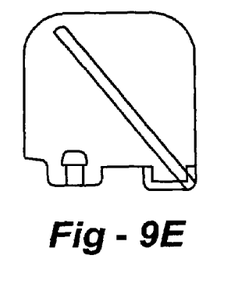
FIG. 9E is an axial cross section of the guide drawn in FIG. 9D.
Figure 9F:
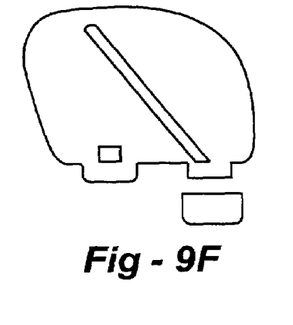
FIG. 9F is an exploded view of the top of the guide and depth stop drawn in FIG. 9E.

FIG. 9E is an axial cross section of the guide drawn in FIG. 9D. A removable depth stop is placed over the slot used to create a spot for the keels. Depth stops of various thickness can be used to accommodate vertebrae of different sizes. FIG. 9F is an exploded view of the top of the guide and depth stop drawn in FIG. 9E.

Figure 10A:
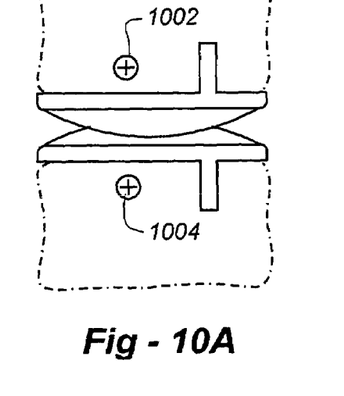
FIG. 10A is an anterior view of the spine, an ADR with oblique keels, and screws.
Figure 10B:
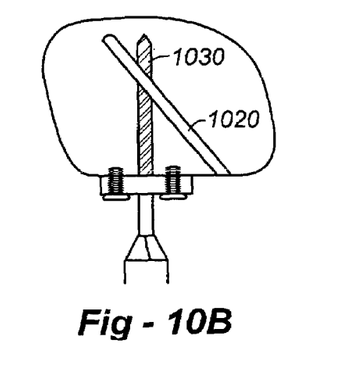
FIG. 10B, a novel drill guide, and a drill.

FIG. 10A is an anterior view of the spine, an ADR with oblique keels, and screws 1002, 1004. The screws are threaded into the keels. The threads of the screws may strip slightly as they enter the holes in the keels. FIG. 10B is a view of the top of the ADR drawn in FIG. 10B, a novel drill guide 1020, and a drill 1030. The removable guide attaches to the front of the ADR. The guide directs the drill into the hole in the keel. A sleeve fits into the guide to accept the drill bit. The hole in the guide that remains after removing the sleeve is used to guide the screw into the hole in the keel.

Figure 11A:
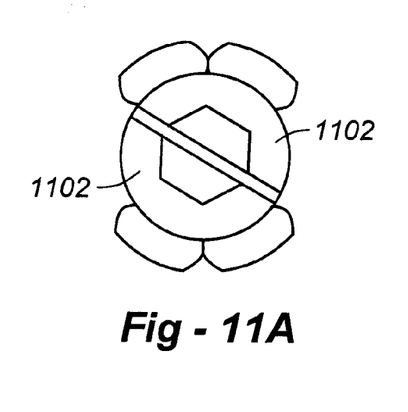
FIG. 11A is a view of the top of a novel locking screw.
Figure 11B:
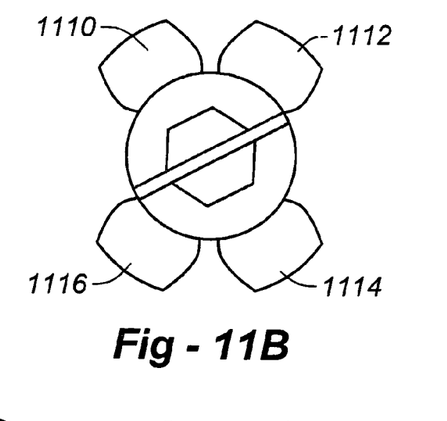
FIG. 11B is a view of the top of the expandable screw drawn in FIG. 11A.
Figure 11C:
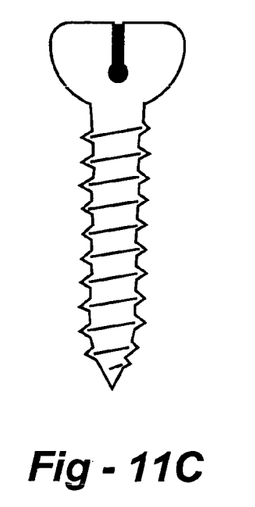
FIG. 11C is a lateral view of the screw drawn in FIG. 11A.
Figure 11D:
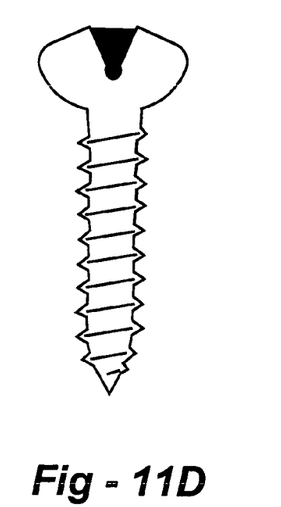
FIG. 11D is a lateral view of the screw drawn in FIG. 11B.
Figure 11E:
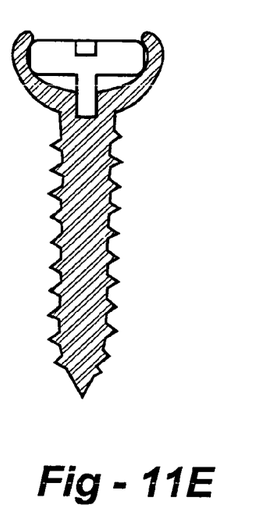
FIG. 11E is a sagittal cross section of the screw drawn in FIG. 11E.
Figures 11F, 11G, 11J:
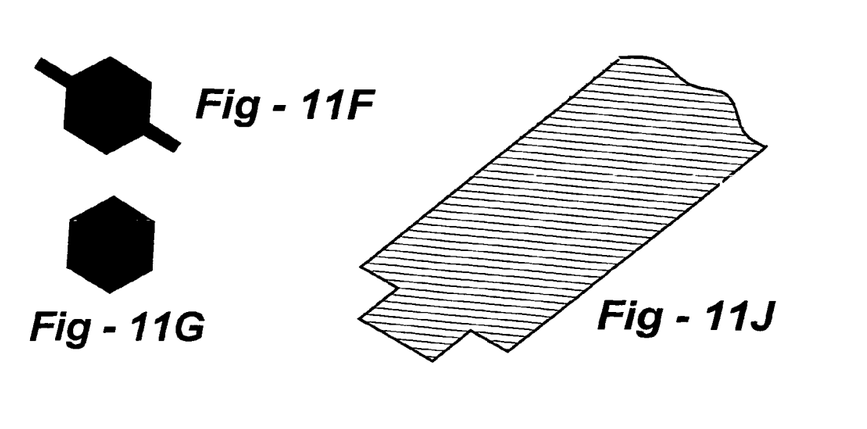
FIG. 11F is a view of the tip of a screw driver that fits into the cam of the screw drawn in FIG. 11A.
FIG. 11G is a view of the tip of a hex head screw driver.
FIG. 11J is a lateral view of a counter rotation tool.

FIG. 11A is a view of the top of a novel locking screw. A cam 1102 can be rotated to expand the head of screw. FIG. 11B is a view of the top of the expandable screw drawn in FIG. 11A. The cam has been rotated 90 degrees to expand portions 1110, 1112, 1114, 1116 of the head of the screw. FIG. 11C is a lateral view of the screw drawn in FIG. 11A. The head of the screw is drawn in its resting shape. FIG. 11D is a lateral view of the screw drawn in FIG. 11B. The head of the screw has been expanded. FIG. 11E is a sagittal cross section of the screw. FIG. 11F is a view of the tip of a screw driver that fits into the cam of the screw drawn in FIG. 11A. The thin projections from the sides of the hex head fit into the slots of the cam. The projections impinge against the side of the screw as the screw driver is rotated. The projections allow advancement of the screw without rotating the cam relative to the screw.

Figure 11H:
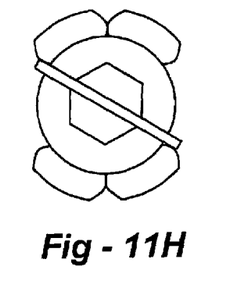
FIG. 11H is the view of the top of the screw drawn in FIG. 11A and the tip of the screw driver drawn in FIG. 11F.

FIG. 11G is a view of the tip of a hex head screw driver. The hex head screw driver is used to rotate the cam without rotating the screw. FIG. 11H is the view of the top of the screw drawn in FIG. 11A and the tip of the screw driver drawn in FIG. 11F. The screw driver is used to rotate the screw and the cam as a unit. The screw is drawn in its contracted shape.

Figure 11I:
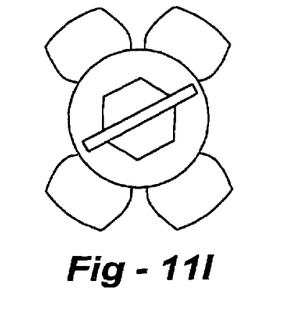
FIG. 11I is a view of the top of the screw drawn in FIG. 11B and the tip of the screw driver drawn in FIG. 11G.
Figure 11K:
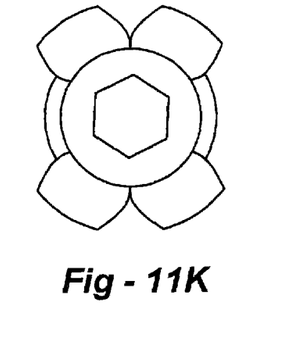
FIG. 11K shows the screw of FIG. 11I cooperating with the tool of FIG. 11J.
Figure 11L:
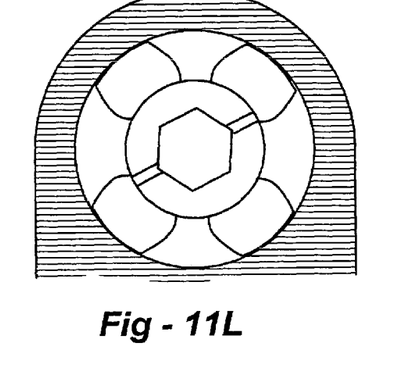
FIG. 11L is an anterior view of a portion of the ADR drawn in FIG. 8A and the screw drawn in FIG. 11B.

FIG. 11I is a view of the top of the screw drawn in FIG. 11B and the tip of the screw driver drawn in FIG. 11G. The hex head screw driver is used to expand the head of the screw by rotating the cam relative to the screw. FIG. 11J is a lateral view of a counter rotation tool. The tool is cannulated. The hex head screw driver fits through the lumen of the counter rotation tool. The projections from the tool engage the sides of the screw. The counter rotation prevents rotation of the screw as the cam is rotated. FIG. 11K shows the screw of FIG. 11I cooperating with the tool of FIG. 11J. FIG. 11L is an anterior view of a portion of the ADR drawn in FIG. 8A and the screw drawn in FIG. 11B. The head of the screw is expanded after the screw is fully seated in the ADR. Expanding the screw locks the screw into the hole of the ADR. The head of the screw could also be expanded into a ring that fits into the hole in the ADR.

Figure 11M:
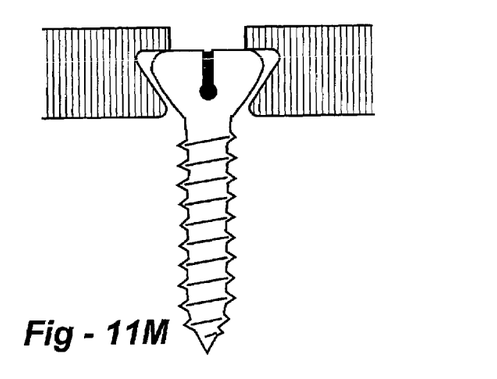
FIG. 11M is an axial cross section of a portion of the ADR drawn in FIG. 8A and the screw drawn in FIG. 11B.

FIG. 11M is an axial cross section of a portion of the ADR drawn in FIG. 8A and the screw drawn in FIG. 11B. The head of the screw is expanded after it is advanced past the first hole in the ADR. The expanded head of the screw becomes locked between the two screw holes in the ADR.

Figures 12A, 12B, 12C:
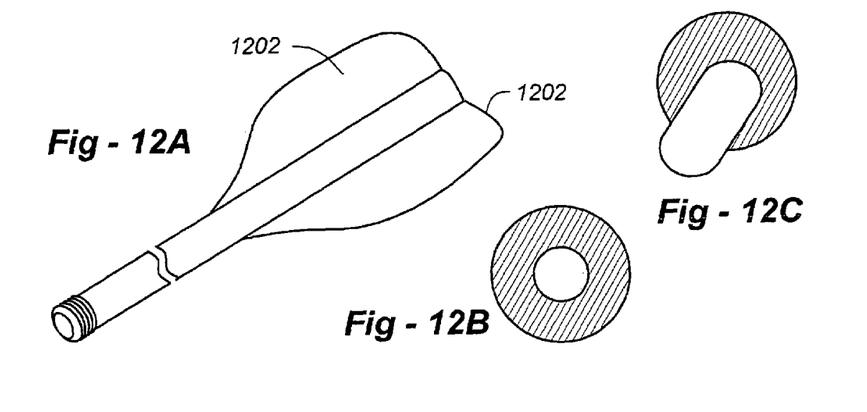
FIG. 12A is sagittal cross section of the insertion instrument drawn in FIG. 6E.
FIG. 12B is a view of the end of the instrument drawn in FIG. 12B.
FIG. 12C is a view of the end of the instrument drawn in FIG. 12B.

FIG. 12A is sagittal cross section of the insertion instrument drawn in FIG. 6E. The shaft of the instrument is preferably radio-opaque, whereas the handle 1202 of the instrument is radiolucent. FIG. 12B is a view of the end of the instrument drawn in FIG. 12B. The instrument is drawn as though it is viewed by a fluoroscope. The circular cross section of the shaft of the instrument indicates the fluoroscope is aligned directly perpendicular to the instrument. Surgeons can use the alignment of the tool and the fluoroscope to help align the ADR. FIG. 12C is a view of the end of the instrument drawn in FIG. 12B. The instrument is no longer circular in cross section. The image of the instrument indicates the fluoroscope is not aligned perpendicular to the instrument and the ADR.

Figure 13:
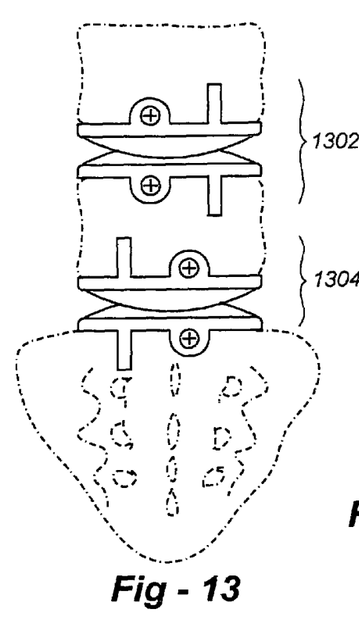
FIG. 13 is an anterior view of the spine, the ADR with oblique keels drawn in FIG. 8A, and an ADR with straight keels.

FIG. 13 is an anterior view of the spine, the ADR 1302 with oblique keels drawn in FIG. 8A, and an ADR 1304 with straight keels. The novel method of pairing ADRs with oblique keels with ADRs with straight keels reduces the risk of fracturing the interposed vertebra. Keels that are parallel and directly across from one another on either vertebral endplate (VEP) may act as wedges to fracture the vertebra. Keels in different locations on the VEPs and that course in different directions reduce the risk of fracturing the vertebra. The locking screw courses an oblique direction in the ADR with straight keels.

Figure 14A:
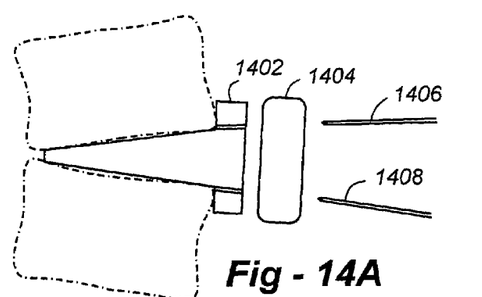
FIG. 14A is a lateral view of the spine, a cutting guide, a depth stop, and saw blades.
Figure 14B:
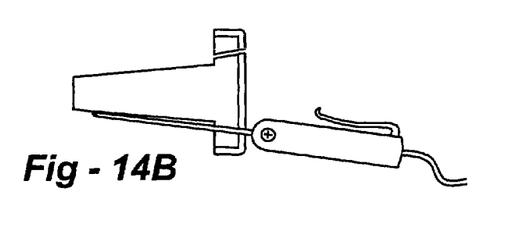
FIG. 14B is sagittal cross section of the guide, depth stop, and saw drawn in FIG. 14A.
Figure 14C:
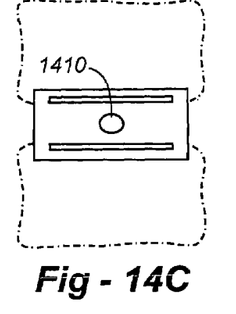
FIG. 14C is an anterior view of the guide drawn in FIG. 14A.

FIG. 14A is a lateral view of the spine, a cutting guide 1402, a depth stop 1404, and saw blades 1406, 1408. The cutting guide was taught in my co-pending U.S. patent application Ser. No. 10/421,436, incorporated herein by reference. Novel depth stops of different thickness are used accommodate vertebrae of different sizes. The removal depth stops work like the stops described in FIG. 9F. The use of saw blades rather than chisels reduces the damage to the vertebrae. FIG. 14B is sagittal cross section of the guide, depth stop, and saw drawn in FIG. 14A. The saw impinges upon the stop to prevent the saw from entering the spinal canal. FIG. 14C is an anterior view of the guide drawn in FIG. 14A. The circle 1410 in the center of the drawing represents the shaft of a removable impaction handle.

Figures 15, 16:
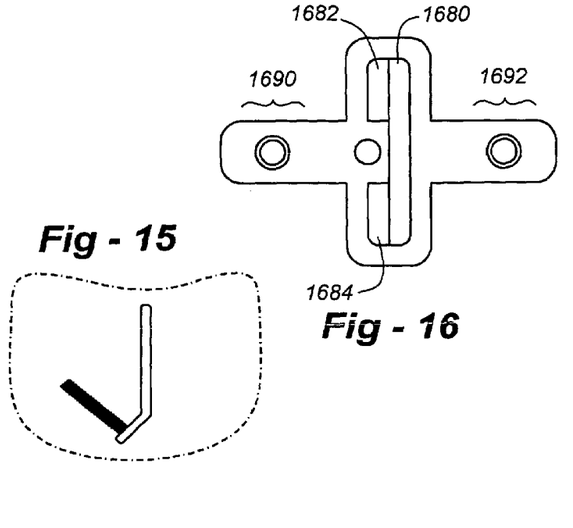
FIG. 15 is a view of the top of an alternative embodiment of the TDR drawn in FIG. 8B.
FIG. 16 is a view of the anterior portion of an alternative embodiment of the guide drawn in FIG. 9A.

FIG. 15 is a view of the top of an alternative embodiment of an ADR having a screw 1550 placed through the anterior portion of the keel. The anterior portion of the keel is angled to ease insertion of the screw. The anterior portion of the keel may have features to cooperate with a drill and a screw guide. The removable guide aligns the hole for the screw and the screw.

FIG. 16 is a view of the anterior portion of an alternative embodiment of a guide used to prepare the vertebrae to receive the embodiment of the ADR drawn in FIG. 15. The slot 1680 is used to guide a saw to prepare the vertebrae to receive the straight portions of the keels. The guide also has areas 1682, 1684 to mill recesses in the vertebrae to accept the angled portions of the keels. The guide also incorporates an alternative embodiment of the partially radiolucent handle drawn in FIG. 6E. Partially radiolucent components are incorporated into the guide (areas 1690, 1692). The partially radiolucent markers help determine if the guide is inserted with the correct axial rotation. The guide is placed properly if radio-opaque circles appear centered in radiolucent circles. The anatomy of the spine, for example the pedicles and the spinous processes of the vertebrae can be used to align the beam of the fluoroscope. The guide can then be aligned with respect to the fluoroscope.

I claim:

1. A artificial disc replacement (ADR) system, comprising: an intradiscal component, including:
    an anterior portion,
    a posterior portion,
    a keel adapted to penetrate a vertebral endplate, the keel having an orientation other than anterior-to-posterior when the component is installed and,
    a screw adapted to penetrate a vertebral body and a portion of the keel.

2. The system of claim 1, further including a guide for aligning the ADR prior to insertion.

3. The system of claim 1, further including a guide for cutting an oblique slot into a vertebral endplate to receive the keel.

4. The system of claim 1, wherein the screw and keel converge.

5. The system of claim 1, wherein the screw includes a mechanism providing a locking relationship with the keel.

6. The system of claim 1, further including:
    an ADR having a screw-capturing portion; and
    a guide for forming a recess associated with the screw-capturing portion.

7. The system of claim 1, for including a guide to direct drill bits and screws through holes in the keel.

8. The system of claim 1, further including a second ADR at a second level having a keel oriented differently from that of the ADR having an orientation other than anterior-to-posterior.

9. The system of claim 1, wherein the ADR includes a non-symmetrical endplate oriented rightwardly of the disc space to decrease the risk of injuring the great vessels.

* * * * *